United States Patent [19]

Wilkens

[11] Patent Number: 4,673,743

[45] Date of Patent: Jun. 16, 1987

[54] PROCESS FOR SEPARATING CAFFEINE FROM CAFFEINE-LOADED ACTIVE CARBON

[75] Inventor: Jochen Wilkens, Bremen, Fed. Rep. of Germany

[73] Assignee: Hag GF Aktiengesellschaft, Bremen, Fed. Rep. of Germany

[21] Appl. No.: 842,848

[22] Filed: Mar. 24, 1986

[51] Int. Cl.[4] ............................................. C07D 473/12
[52] U.S. Cl. ...................................... 544/275; 544/274
[58] Field of Search .................................. 544/274, 275

[56] References Cited

U.S. PATENT DOCUMENTS 4,540,784  9/1985  Vitzhum et al. .................... 544/275

Primary Examiner—Nicholas S. Rizzo
Attorney, Agent, or Firm—Linn I. Grim; Daniel J. Donovan

[57] ABSTRACT

The invention relates to a process for separating caffeine from caffeine-loaded active carbon in which a circulated inert gas sweeping stream is passed rectangularly through the stream of active carbon at a temperature of 350° to 450° C., and the caffeine desorbed from the active carbon is precipitated in the form of solid particles by quenching the inert gas sweeping stream, and separated.

9 Claims, 1 Drawing Figure

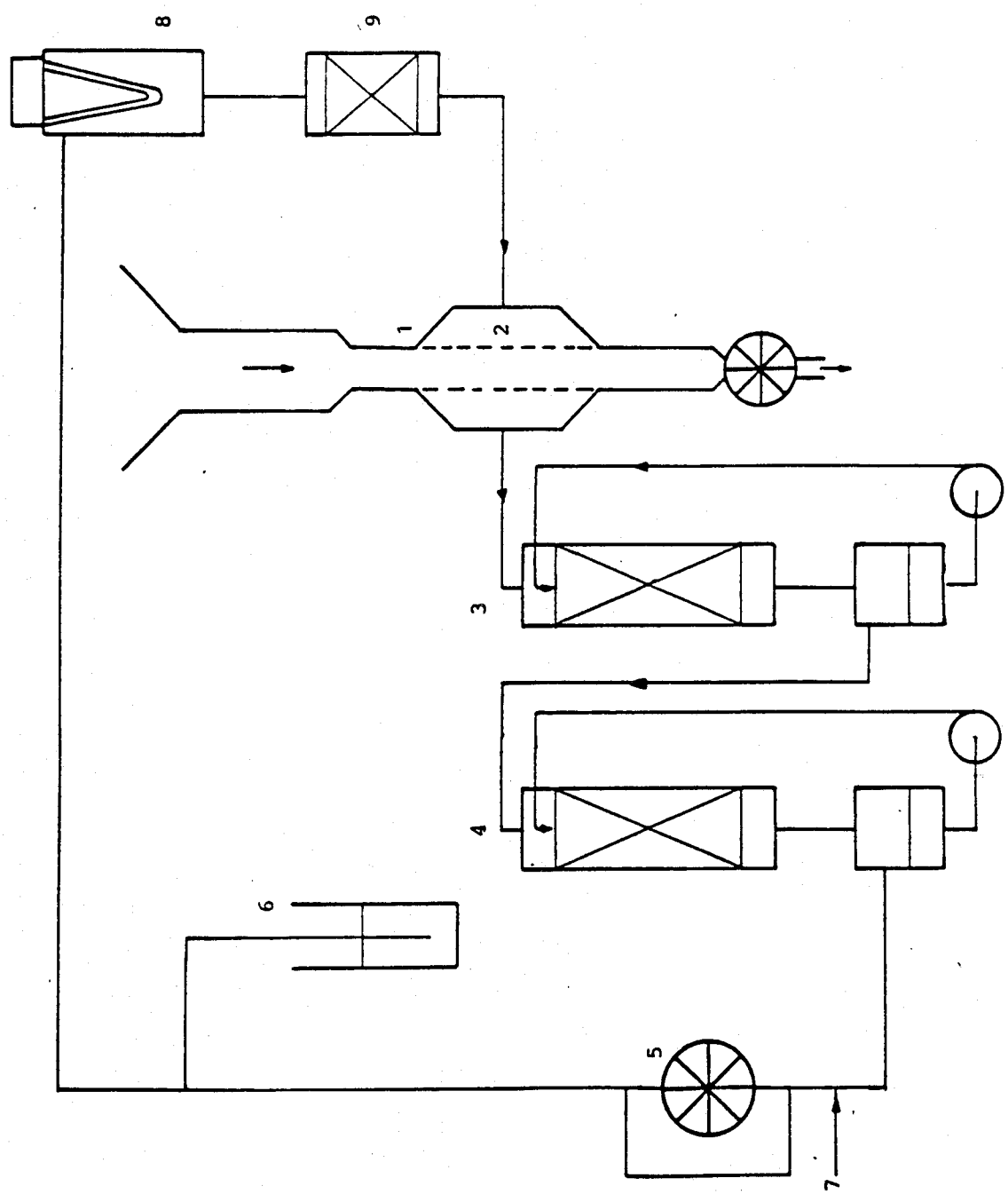

PROCESS FOR SEPARATING CAFFEINE FROM CAFFEINE-LOADED ACTIVE CARBON

The decaffeination of vegetable products is considerably significant for reasons of health. The caffeine produced as by-product can be profitably sold, too.

In several decaffeination processes the pretreated coffee beans are decaffeinated by means of organic solvents. The solvent is recovered, for example, by distillation in the course of which caffeine is obtained as by-product.

In order to avoid any possible contamination of the vegetable material by solvent residues, the hygienically unobjectionable carbon dioxide has recently been used as extractant (German Patents Nos. 2,005,293 and 2,212,281). In these processes the carbon dioxide solvent is freed from dissolved caffeine by means of active carbon.

Before re-use of used active carbon there normally is carried out a pyrolysis of the adsorbed substances followed by thermal reactivation. In view of the usefulness of caffeine such a procedure is uneconomical.

Therefore, efforts have been made to recover the adsorbed caffeine. In selecting measures for desorption of caffeine one must bear in mind that active carbon is a very effective adsorbent, which renders desorption difficult. Moreover, the use of agents that pose a health problem must be avoided, because the very extraction with carbon dioxide permits the exclusion of such agents. For efficient and economical regeneration of the active carbon the solvent should have a high solubilizing capacity for the adsorbate and good transportation characteristics with respect to the adsorbate; moreover, the mixture should thereafter be easily separable.

According to the teaching of German Offenlegungsschrift No. 2,544,116, the adsorbate is desorbed with supercritical gases, especially with carbon dioxide. In this process the dissolved adsorbate must, in turn, be removed from the dissolving gas.

U.S. Pat. No. 4,298,736 describes a process in which caffeine adsorbed to active carbon is desorbed with a liquid solvent admissible for foods, which may be an organic acid or an alcohol. The process is preferably carried out above 100° C. with glacial acetic acid or with azeotropic mixtures of glacial acetic acid and second components.

After regeneration of the active carbon with nonvolatile solvents, however, the solvent must be separated from the active carbon in any event, e.g. with steam. This necessitates an additional step.

It is the object of the invention to provide a simple and economical process for recovering caffeine adsorbed to active carbon and for simultaneously regenerating the active carbon, in which desorption of caffeine from the active carbon is to be effected with an agent that is unobjectionable under the health aspect.

This object is realized by a process in which caffeine is desorbed from the active carbon in that a circulated inert gas sweeping stream is passed rectangularly through the stream of active carbon at a temperature of 350° to 450° C., and the caffeine desorbed from the active carbon is precipitated by quenching the inert gas sweeping stream in the form of solid particles, and separated.

A suitable apparatus for carrying out the process is schematically illustrated in the drawing.

In the process of the invention an inert gas maintained at a temperature of 350° to 450° C. sweeps rectangularly through the active carbon loaded with caffeine. The caffeine is thereby desorbed from the active carbon and is removed from the active carbon bed by the inert gas sweeping stream. Thereafter the inert gas sweeping stream is quenched whereby the caffeine precipitates in the form of solid particles and is separated by suitable measures. The inert gas sweeping stream is then reheated and recycled to the active carbon bed for further desorption.

It has been an essential aspect of the invention to separate the caffeine from the active carbon in high yields. Initial attempts to pass the inert gas sweeping stream in counterflow through the active carbon did not bring about satisfactory results. The caffeine yield could not be increased substantially above 50%. Presumably the caffeine already desorbed by the counterflow is again contacted with less hot active carbon and thus re-adsorbed by the latter. After repeated desorption and adsorption of the caffeine increased decomposition presumably takes place. Experiments carried out in this connection with inert carrier materials (glass beads) loaded with caffeine seem to confirm this presumption. The caffeine yield in these cases amounted to about 86%. In the making of the present invention it was found that excellent yields can be obtained if the hot inert gas sweeping stream is passed rectangularly through the loaded active carbon. A suitable apparatus for carrying out the process of the invention consists of a vertical shaft with defined bed thickness through which the loaded active carbon slides from top downwardly. The heated inert gas sweeping stream is passed horizontally through the active carbon by way of perforated metal sheets in a predetermined region of the shaft.

Perforated sheets with an aperture diameter of about 1.5 mm have proved to be favorable. The open surface provided by the perforated sheets should be about 50%. The outer shaft walls can be additionally heated with a heating jacket, which is not necessary, in general, if care is taken for adequate insulation. Such an apparatus will be designated hereafter as crossflow furnace.

The bed thickness of the stream of active carbon influences the caffeine yield. In general, it can be said that with increasing bed thickness the caffeine yield decreases. On the other hand, with very shallow beds the flow resistance of the bed becomes non-uniform and thus the flow becomes unequal, owing to the particle size of the active carbon employed. Bed thicknesses of 20 to 60 mm, preferably 25 to 50 mm, have proved to be practicable.

In order to obtain good caffeine yields, the residence time of the active carbon in the part of the apparatus swept by the inert gas sweeping stream should be about 10 to 60 minutes, preferably 20 to 30 minutes. The flow rate of the inert gas sweeping stream can be 2 to 10 cm/sec., preferably from 5 to 7 cm/sec. (standard conditions, empty crossflow furnace).

Also the initial moisture content of the loaded active carbon affects the caffeine yield. The initial moisture should be less than 15%, preferably less than 1%.

As mentioned before, the temperature during desorption is 350° to 450° C. Preferably said temperature is within a range from 410° to 420° C. Under these and the above mentioned conditions very high yields are attainable. The residual caffeine content on the active carbon is as low as 1 to 2%, based on an initial caffeine content of 100%.

Any inert gas can be used as sweeping gas. Carbon dioxide and nitrogen are especially suited. Also mixtures of the two gases obtained as combustion gases, can be successfully employed. Furthermore, air can be used as sweeping gas whose oxygen content has previously been converted to CO and $CO_2$, preferably by reaction with active carbon. To this end the air is preferably passed through a bed of active carbon upstream of the crossflow furnace. The atmospheric oxygen entrained into the crossflow furnace together with the active carbon is no nuisance, as it is instantly reacted to CO and $CO_2$ by the hot carbon. However, major inflow of air through leaks ought to be avoided, as the active carbon may start burning at temperatures higher than 350° C. In order to completely exclude this hazard, it is suitable, in any event, to pass the inert gas sweeping stream through a bed of unloaded active carbon before its entry into the crossflow furnace, even if pure nitrogen or carbon dioxide gas is used, for example.

Said active carbon bed must be renewed from time to time. In general, care should be taken that the inert gas sweeping stream contains less than 100 ppm (v/v) of oxygen.

It was experimentally found that the caffeine yields were markedly higher with the use of active carbons having other substances adsorbed thereto (e.g. other coffee ingredients) in addition to caffeine. Therefore, attempts were made to provide the loaded active carbons with such additional substances prior to thermal desorption. A marked increase in caffeine yield was attained by spraying the active carbon, for example, with low-viscosity paraffin oil (white oil, see DAB 7) and coffee oil (press water oil, a waste product from the production of instant coffee). The quantity of sprayed liquid amounted up to 10%, preferably it is 2 to 3%. Thereby the caffeine yield could be increased up to 10%. In lieu of paraffin oil or coffee oil also other coffee ingredients can be sprayed, of course.

The inert gas sweeping stream loaded with caffeine is quenched after it has left the crossflow furnace. The caffeine is thereby obtained in the form of fine particles. Quenching is preferably carried out with cold water. Thereby the caffeine is washed out of the inert gas sweeping stream. The particles are then retained by ultrafine fiber filters, e.g. filters made from glass or quartz fibers. The scrubbing water is circulated concurrently with the inert gas sweeping stream. By contacting the scrubbing water with the hot inert gas sweeping stream the scrubbing water heats up to a certain degree. Said scrubbing water redissolves the caffeine retained by the fine fiber filters. In continuous operation caffeine concentrations up to 100 g/l can be attained in the scrubbing water. For recovery of crude caffeine the scrubbing water can be directly passed to a crystallization stage.

Since the inert gas sweeping stream contains active carbon dust and pyrolysis products of other coffee ingredients, in addition to caffeine, which may result in clogging of the fiber filters, a second gas scrubber filled with coarse granules having no clogging tendency (e.g. Raschig rings) is positioned upstream. This filter is flushed with a separare scrubbing water circuit.

The throughput of sweeping gas through the filters is about 2000 $[m^3/(m^2 \times h)]$ while the scrubbing water load on the filters is approximately 20 $[m^3/(m^2 \times h)]$.

In lieu of the described filter system also single-stage gas scrubbers can be employed. To this end a gas scrubber commercially availably by the name "Aspirotor"-Gasreiniger has proved to be especially advantageous. In this gas scrubber the inert gas sweeping stream passes through a cylindrical rotating filter, while in counterflow water is sprayed from the interior through the filter. The fine caffeine particles are precipitated outside the rotating filter by contact with the cold scrubbing water and are precipitated at the filter. The water passing from the interior outwardly washes the caffeine particles, and also any deposited active carbon dust and pyrolysis products, away so that the rotating filter cannot be clogged. However, within the water circuit of such a single-stage gas scrubber an additional coarse filter ought to be provided in order to trap coarser particles (active carbon dust, pyrolysis products).

Hereafter the apparatus, which is schematically illustrated by the FIGURE and which is suited for carrying out the process of the invention, will be explained in more detail.

The caffeine-loaded active carbon slides from a storage bin of the crossflow furnace 1 through the desorption zone 2 proper, where it is contacted with the hot inert gas sweeping stream for desorption of the caffeine. The inert gas sweeping stream enters the interior of the crossflow furnace 1 through perforated metal sheets, passes through the active carbon, and leaves said zone again through perforated metal sheets. After having left the desorption zone 2, the active carbon is discharged from the crossflow furnace 1 by a cellular wheel sluice or the like.

The caffeine-loaded inert gas sweeping stream passes from the crossflow furnace 1 to a gas scrubber 3 where it is cooled by the circulating scrubbing water to temperatures below 100°. In the gas scrubber 3 the inert gas sweeping stream together with the scrubbing water passes through a first filter which predominantly retains active carbon dust and other coarser particles. Thereafter the inert gas sweeping stream passes into the gas scrubber 4 where it is cooled further. The caffeine precipitating in the two gas scrubbers 3 and 4 is retained by a fine fiber filter in the gas scrubber 4 and is gradually redissolved by the circulated and slowly heating scrubbing water. As mentioned above, thereby concentrations up to 100 g/l of caffeine can be reached; the caffeine can be recovered in a separate apparatus, not shown, by crystallization. About 10% of the total caffeine yield are recovered in the first gas scrubber 3.

After the inert gas sweeping stream has left the gas scrubber 4, it is conveyed by means of a gas circulating pump 5 to the gas heater 8; before reentering the crossflow furnace 1 the active carbon passes through a preliminary filter 9 for reduction of residual oxygen.

Upstream of the gas circulating pump 5 there is a valve 7 for feeding additional inert gas. Downstream of the gas circulating pump 5 there is a pressure relief means 6.

The bed of loaded active carbon in the storage bin of the crossflow furnace 1 must be sufficiently high to prevent breakthrough of hot gas. In this way gas-tight introduction of active carbon into the crossflow furnace 1 can be avoided. The entire process is operated such that in the desorption zone 2 of the crossflow furnace 1 there prevails superatmospheric pressure of only a few millibars.

The following examples are given for further explanation of the invention. For the operation of the process of the invention an apparatus was used similar to that schematically illustrated in the drawing. In all instances the sweeping gas load on the filters was about 2000 m³/m²×h, while the scrubbing liquid load was about 20 m³/m²×h. For all the tests the same type of active carbon was used, which was loaded with caffeine. The bed thickness of the active carbon stream was 40 mm in each instance. In the evaluation of the results the total quantity of caffeine extractable from the active carbon with solvent corresponds to 100%. As yield (caffeine) there is stated the amount of caffeine found in the scrubbing liquid, based on recoverable amount of caffeine. As residue (caffeine on the active carbon) there is stated the amount still present on the active carbon after it passed through the crossflow furnace, also based on total recoverable caffeine. The loss of caffeine results from 100 - (residue + yield). In examples 1 to 4 the initial moisture content of the loaded active carbon was about 7.7%. The sweeping gas employed was air.

EXAMPLE 1

In this example the influence of the desorption temperature (gas discharge temperature) on the yield was examined. The flow rate of the inert gas sweeping stream was 5.6 cm/sec., and the residence time of the active carbon in the desorption zone was about 27 minutes. The obtained results are compiled in the following Table I.

TABLE I

| T in °C. | Yield in % | Residue in % | Loss in % |
| --- | --- | --- | --- |
| 326 | 49.7 | 25.5 | 24.8 |
| 340 | 55.0 | 19.2 | 25.8 |
| 370 | 76.3 | 2.6 | 21.1 |
| 416 | 76.4 | 0.7 | 22.9 |
| 460 | 58.9 | 0.0 | 41.1 |

EXAMPLE 2

In this example the influence of the flow rate v through the desorption zone was examined. The flow rate was measured before the entry into the crossflow furnace. The residence time of the active carbon stream in the desorption zone was about 27 minutes. The temperature of the inert gas sweeping stream leaving the crossflow furnace was 410° C.

The results are compiled in the following Table II.

TABLE II

| v in cm/sec | Yield in % | Residue in % | Loss in % |
| --- | --- | --- | --- |
| 2.8 | 56.7 | 4.2 | 41.1 |
| 4.2 | 73.0 | 1.3 | 25.7 |
| 5.6 | 75.0 | 2.6 | 22.4 |

EXAMPLE 3

In this example the influence of the time of residence of the loaded active carbon in the desorption zone was examined. The temperature in the desorption zone, as measured on the inert gas sweeping stream leaving the desorption zone, was 410° C. The flow rate of the inert gas sweeping stream was 5.6 cm/sec. The results of the tests are compiled in the following Table III.

TABLE III

| t in min | Yield in % | Residue in % | Loss in % |
| --- | --- | --- | --- |
| 40 | 62.8 | 0.0 | 37.2 |
| 27 | 74.2 | 0.7 | 25.1 |
| 20 | 73.0 | 1.3 | 25.7 |

EXAMPLE 4

By means of several tests the influence of the caffeine load and the type of decaffeinated coffee was examined. In a first sample the degree of loading of the active carbon with caffeine was 15.6%. The caffeine originated from Robusta coffee. In a second sample the degree of loading with caffeine was 3.2, and the caffeine originated from Arabica coffee. In a third sample the degree of caffeine loading was 9.5%, and the caffeine also originated from Arabica coffee.

The desorption temperature was 410° C., and the time of residence of the active carbon in the desorption zone was about 27 minutes. The flow rate of the inert gas stream through the desorption zone was 5.6 cm/sec.

No influence of the degree of loading and the type of coffee on the yield, residue, and loss could be detected.

EXAMPLE 5

In this example the influence of the initial moisture content was examined. The temperature of the desorption zone was 410° C. The time of residence of the active carbon in the desorption zone was about 27 minutes, and the flow rate of the sweeping gas through the desorption zone was 5.6 cm/sec. The results are compiled in the following Table IV.

TABLE IV

| Moisture in % | Caffeine Yield in % |
| --- | --- |
| 15.8 | 69.0 |
| 7.7 | 75.0 |
| <1.0 | 85.3 |

I claim:

1. A process for separating caffeine from caffeine-loaded active carbon comprising: (1) passing an inert gas stream at temperatures from about 350° C. to about 450° C. rectangularly through said caffeine-loaded active carbon which desorbs said caffeine from said active carbon; (2) precipitating said caffeine by quenching said caffeine containing inert gas stream.

2. The process of claim 1 wherein the precipitated caffeine is recovered from the quenched inert gas stream.

3. The process of claim 1 wherein the temperature of said inert gas is from about 410° C. to about 420° C.

4. The process of claim 1 wherein the inert gas is selected from the group consisting of carbon dioxide, nitrogen, carbon monoxide or mixtures thereof.

5. The process of claim 1 wherein the oxygen content in said inert gas stream is below about 100 parts per million.

6. The process of claim 1 wherein the initial moisture content of said caffeine-loaded active carbon is below about 15 weight percent based on said caffeine-loaded active carbon.

7. The process of claim 1 wherein the initial moisture of said caffeine-loaded active carbon is below about one weight percent based on said caffeine-loaded active carbon.

8. The process of claim 1 wherein addition to the caffeine, the active carbon contains up to about 10 weight percent adsorbed thereto other substances selected from the group consisting of paraffin oil, coffee oil, other coffee ingredients or mixtures thereof.

9. The process of claim 1 wherein the caffeine-containing inert gas stream is quenched by intensive mixing with water whereby the caffeine is washed out of the inert gas sweeping stream.

* * * * *